United States Patent [19]

Okazaki

[11] Patent Number: 5,150,713
[45] Date of Patent: Sep. 29, 1992

[54] METHOD AND SYSTEM FOR CONTROLLING SHOCK WAVE IRRADIATION IN A SHOCK WAVE THERAPY APPARATUS

[75] Inventor: Kiyoshi Okazaki, Tochigi, Japan

[73] Assignee: Kabushiki Kaisha Toshiba, Kawasaki, Japan

[21] Appl. No.: 569,909

[22] Filed: Aug. 20, 1990

[30] Foreign Application Priority Data

Aug. 21, 1989 [JP] Japan .................................. 1-212942

[51] Int. Cl.⁵ .............................................. A61B 17/22
[52] U.S. Cl. .............................. 128/660.03; 128/24 EL
[58] Field of Search ........ 128/24 AA, 24 EL, 660.01, 128/660.03

[56] References Cited

U.S. PATENT DOCUMENTS

| Re. 33,590 | 5/1991 | Dory | 128/660.03 |
|---|---|---|---|
| 4,191,189 | 3/1980 | Barkan . | |
| 4,787,394 | 11/1988 | Ogura | 128/660.03 |
| 4,791,915 | 11/1988 | Barsotti et al. | 128/24 AA |
| 4,917,095 | 4/1990 | Fry et al. | 128/24 EL |
| 4,928,671 | 5/1990 | Reichenberger et al. | 128/24 EL |
| 4,932,414 | 6/1990 | Coleman et al. | 128/660.03 |
| 4,942,868 | 7/1990 | Vago | 128/24 AA |
| 4,942,878 | 7/1990 | Dory | 128/660.03 |
| 4,958,639 | 9/1990 | Uchiyama et al. | 128/660.03 |
| 4,986,275 | 1/1991 | Ishida et al. | 128/660.03 |

Primary Examiner—Lee S. Cohen
Assistant Examiner—K. M. Pfaffle
Attorney, Agent, or Firm—Finnegan, Henderson, Farabow, Garrett and Dunner

[57] ABSTRACT

In a shock wave therapy apparatus, shock wave irradiation conditions, such as the number of shock wave irradiations, a pulse rate, a driving voltage, and the number of pause shots, are set by a setting unit in accordance with the position and size of a calculus in a subject which are acquired by an ultrasonic tomographic image. Irradiation of shock waves by a shock wave applicator starts according to the set shock wave irradiation conditions, and the ultrasonic tomographic image and the corresponding irradiation condition data are displayed on a display unit during shock wave irradiation. When the number of shock wave irradiations reaches the number of pause shots, the shock wave irradiation is temporarily stopped. Then, the focus point of a shock wave is moved on the basis of the ultrasonic tomographic image and irradiation condition data displayed on the display unit. When the shock wave irradiation is completed, a therapy record of the subject is printed out by an output unit.

24 Claims, 8 Drawing Sheets

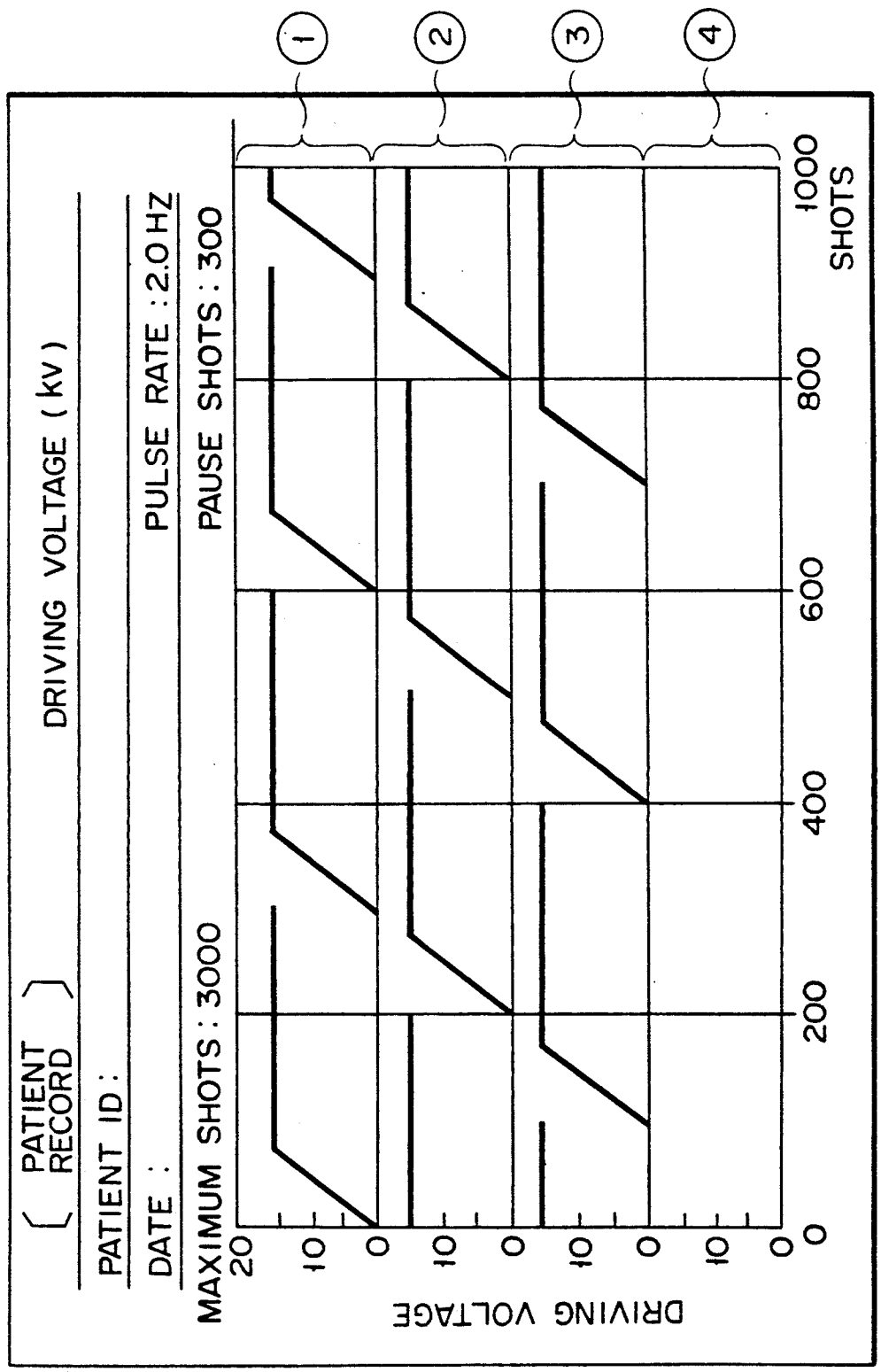
F I G. 4

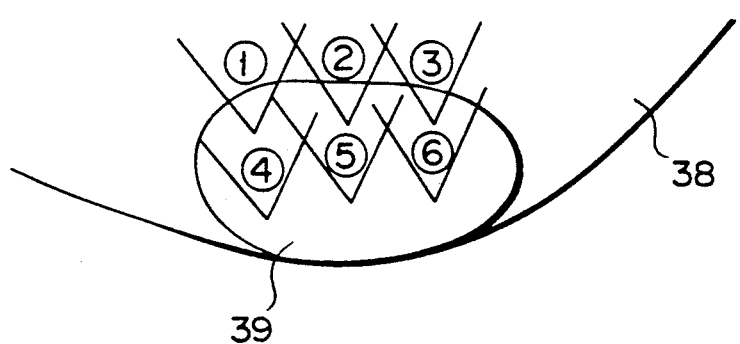
F I G. 6

METHOD AND SYSTEM FOR CONTROLLING SHOCK WAVE IRRADIATION IN A SHOCK WAVE THERAPY APPARATUS

BACKGROUND OF THE INVENTION

1. Field of the Invention

The present invention relates to a method and system for controlling shock wave irradiation in a shock wave therapy apparatus.

2. Description of the Related Art

Recently, shock wave therapy apparatuses have been developed which irradiate a shock wave (ultrasonic wave) to a subject to be examined to disintegrate a calculus or the like in the subject.

If a shock wave is irradiated toward normal tissue, not a calculus, an adverse effect on the subject often results, such as damage to the normal tissue. In this respect, therefore, it is important to disintegrate a calculus with the minimum adverse effect on the subject. If a large abnormal portion such as a calculus exists in the subject, (often its size varies depending on the subject), it is necessary to make a therapy plan to disintegrate the calculus by applying a shock wave to various portions of the calculus, carry out the calculus disintegration based on the therapy plan. With the use of the conventional shock wave therapy apparatuses, however, it is difficult to formulate a therapy plan and carry out the calculus disintegration based thereon.

There is therefore a demand for a shock wave therapy apparatus capable of controlling the irradiation of a shock wave so as to disintegrate a calculus based on a therapy plan.

SUMMARY OF THE INVENTION

It is an object of the present invention to provide a method and system for controlling shock wave irradiation in an shock wave therapy apparatus.

According to first aspect of the present invention, there is provided a system for controlling shock wave irradiation in a shock wave therapy apparatus, the system comprising:

acquiring means for acquiring an ultrasound tomogram image of a subject;

displaying means for displaying the acquired ultrasound tomogram image to detect an irradiation portion within the subject;

irradiating means for irradiating shock waves to the detected irradiation portion;

setting means for setting irradiation conditions; and controlling means for controlling the irradiating means in accordance with the set irradiation conditions to irradiate the shock waves to the irradiation portion during a plurality of irradiation periods determined by the set irradiation conditions.

According to second aspect of the present invention, there is provided a system for controlling shock wave irradiation in a shock wave therapy apparatus, the system comprising:

acquiring means for acquiring an ultrasound tomogram image of a subject;

displaying means for displaying the acquired ultrasound tomogram image to detect an irradiation portion within the subject;

irradiating means for irradiating shock waves to the detected irradiation portion; and controlling means for controlling the irradiating means to irradiate the shock waves to the irradiation portion during a desired irradiation period, wherein state data representing an irradiation state corresponding to the displayed ultrasound tomogram image is displayed with the ultrasound tomogram image by the displaying means during the shock waves are irradiated to the irradiation portion.

According to third aspect of the present invention, there is provided a system for controlling shock wave irradiation in a shock wave therapy apparatus, the system comprising:

acquiring means for acquiring an ultrasound tomogram image of a subject;

displaying means for displaying the acquired ultrasound tomogram image to detect an irradiation portion within the subject;

irradiating means for irradiating shock waves to the detected irradiation portion;

controlling means for controlling the irradiating means to irradiate the shock waves to the irradiation portion during a desired irradiation period; and outputting means for outputting an irradiation record representing an irradiation result after an irradiation of the shock waves to the irradiation portion is completed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

FIG. 4 is a diagram showing a therapy record printed out by an output unit of the present system;

FIG. 6 is a diagram for explaining the movement of a focusing point of a shock wave to a subject under therapy.

DETAILED DESCRIPTION OF THE PREFERRED EMBODIMENTS

A preferred embodiment of this invention will now be described referring to the accompanying drawings.

Figure 1:
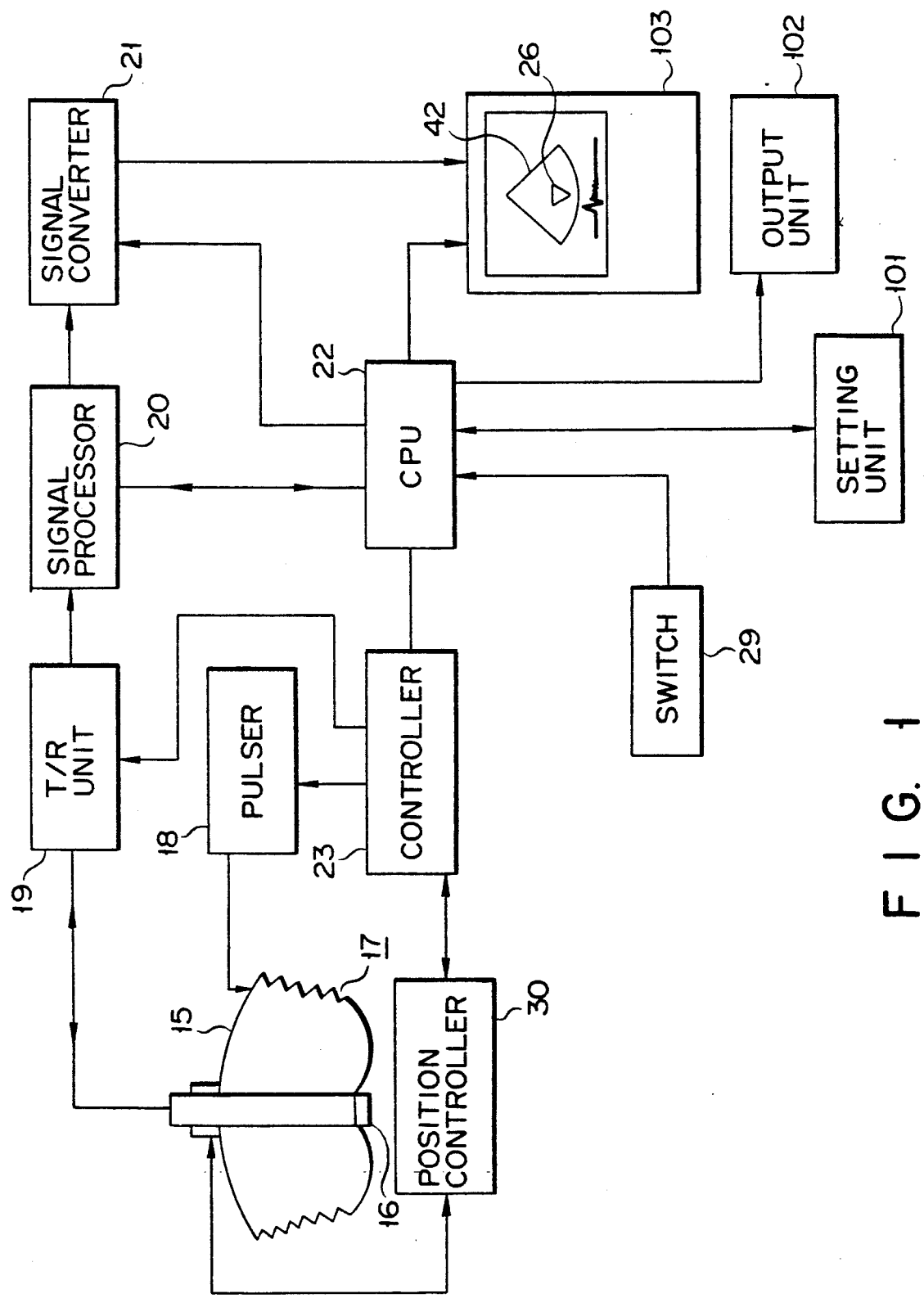
FIG. 1 is a block diagram illustrating the arrangement of a shock wave therapy system embodying the present invention.

A shock wave therapy system as illustrated in FIG. 1 comprises a shock wave applicator 17, a pulser 18, a transmitting/receiving (T/R) unit 19, a signal processor 20, a signal converter 21, a CPU (Central Processing Unit) 22, a controller 23, a switch 29, a position controller 30, a setting unit 101, an output unit 102, and a display unit 103.

The shock wave applicator 17 includes a shock wave transducer 15 for irradiating a shock wave and an ultrasonic transducer 16 for transmitting and receiving an ultrasonic wave having a frequency range different from that of the shock wave from the shock wave transducer 15.

The pulser 18 supplies a pulse signal to the shock wave transducer 15.

The T/R unit 19 outputs a pulse signal to the ultrasonic transducer 16 to execute sector scanning and receives a signal from the ultrasonic transducer 16 in the sector scanning.

The signal processor 20 detects the amplitude of a signal from the T/R unit 19

The CPU 22 controls the individual sections of the system.

The controller 23 controls the signal transmission/reception timing for the pulser 18, the T/R unit 19; and the signal processor 20.

The signal converter 21 including, for example, a digital scan converter, performs a signal conversion process for converting a signal from the signal processor 20 into a video signal.

The display unit 103 including, for example, a TV monitor, displays an ultrasonic tomographic image (sector scan image) including the surface of a subject, kidneys, a calculus, and a shock wave focus point marker 26 indicating an irradiation region of a shock wave, etc., based on the video signal from the signal converter 21. As will be described later, the display unit 103 also displays data indicating the shock wave irradiation conditions according to the ultrasonic tomographic image displayed thereon.

The switch 29 is used to set the timing for generating a pulse signal supplied to the shock wave transducer 15 from the pulser 18.

The position controller 30 controls the relative position of the ultrasonic transducer 16 to the shock wave transducer 15.

The setting unit 101 is used to set the shock wave irradiation conditions, such as the number of shock wave irradiations, the rate of shock wave irradiation (hereinafter referred to as the pulse rate), a shock wave driving voltage, and the number of pause shots. The number of shock wave irradiations represents the number of shock waves to be irradiated until a calculus disintegration is completed. The pulse rate is the number of shock wave irradiations per unit time; for example, when the pulse rate is 2 Hz, two shock waves per second are irradiated to the subject. The number of pause shots corresponds to the interval for calculus disintegration by shock waves; for example, shock wave irradiation is temporarily stopped when the number of pause shots is 300, that is, the number of shock waves reaches 300. In short, the shock wave irradiation is controlled on the basis of the shock wave irradiation conditions set by the setting unit 101.

The output unit 102 outputs (e.g., prints out) record data of shock waves actually irradiated to the subject. The print out record data is used as a therapy record or history. The output unit 102 can also print out an image and the like displayed on the display unit 103 (described later). When a predetermined switch included in the switch 29 is on, the therapy record or the like is printed out.

The shock wave applicator 17 will be described in detail below.

Figure 2:
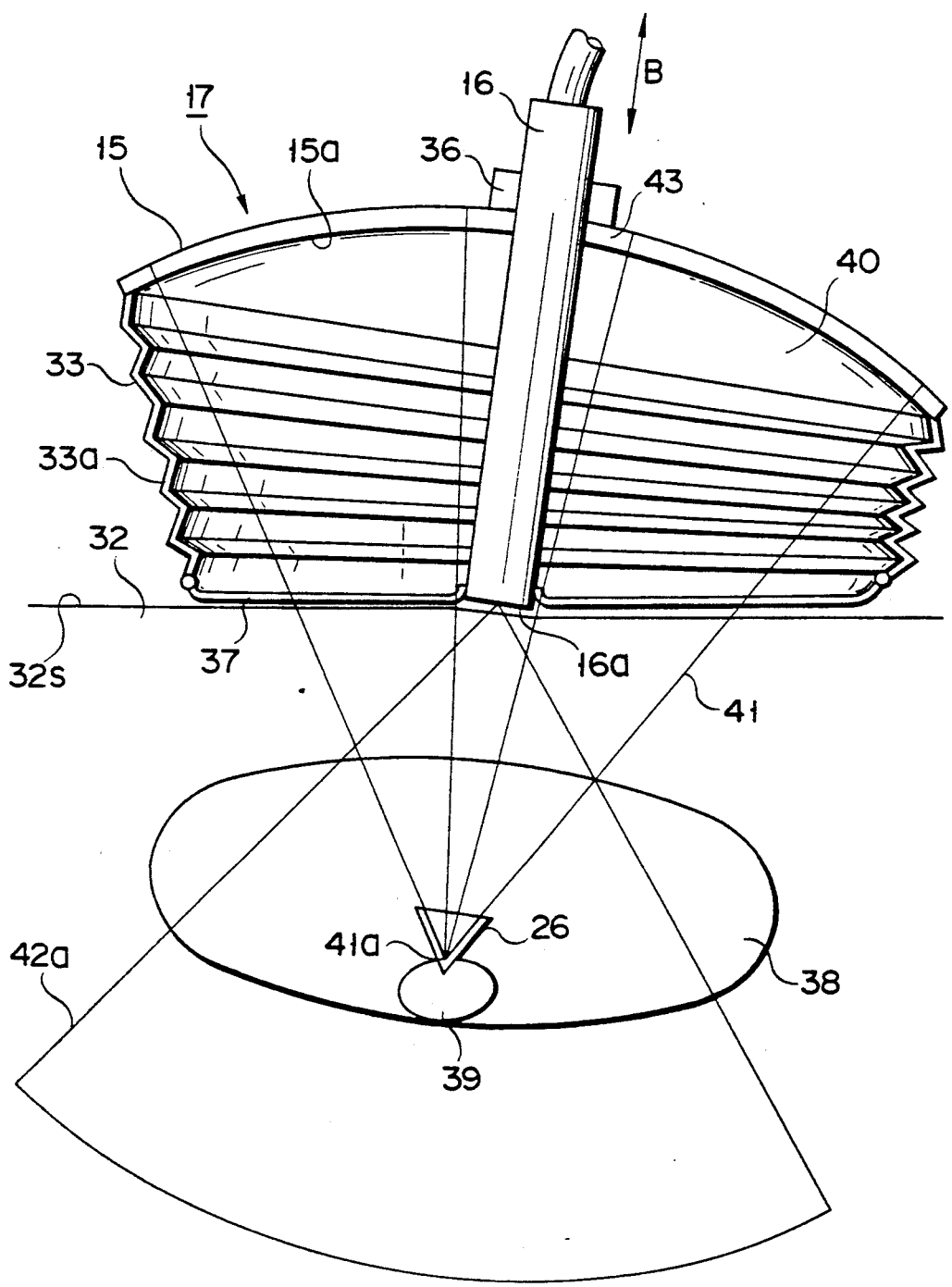
FIG. 2 is a diagram showing the structure of a shock wave applicator of the present system.

Referring to FIG. 2, the shock wave applicator 17 comprises the shock wave transducer 15 and the ultrasonic transducer 16.

The shock wave transducer 15 generates a shock wave, for example, a high-energy ultrasonic wave converging on a focus point 41a in a subject 32. The shock wave transducer 15 is a concave transducer having a predetermined curvature.

The ultrasonic transducer 15 is disposed out of a shock wave irradiating region 41 extending from a shock wave irradiating surface 15a to the focus point 41a. when an ultrasonic transmitting/receiving face 16a of the ultrasound transducer 16 contacts with the surface 32a of the subject 32, an ultrasonic tomographic image (sector scanned image) in a sector scan region 42a including the focus point 41a is obtained. The ultrasound transducer 16 is attached to the center portion of the shock wave transducer 15 by using a transducer moving section 36, and is movable in the direction B in FIG. 2.

The transducer moving section 36 moves the ultrasonic transducer 16 to a predetermined position in the direction B based on a control signal from the position controller 30. For instance, the relative position between the transducers 15 and 16 is controlled by adjusting the rotational angle of a motor (not shown) having its drive shaft connected to a pinion gear (not shown) that engages with a rack member (not shown) fixed to the side of the ultrasound transducer 16. A water tank 33 filled with water as a shock wave propagating liquid is provided in the shock wave transducer 15. The water tank 33 has a cylindrical or conical shape with a bottom whose size is substantially equal to the outer diameter of the shock wave transducer 15. The water tank 33 has a bellows 33a formed at its side; the bellows 33a can be stretched or shrunk in the direction B or in a direction having a predetermined angle to the direction B. A bottom 37 of the water tank 33 is formed by a thin film having an acoustic impedance nearly equal to that of water.

Figure 3:
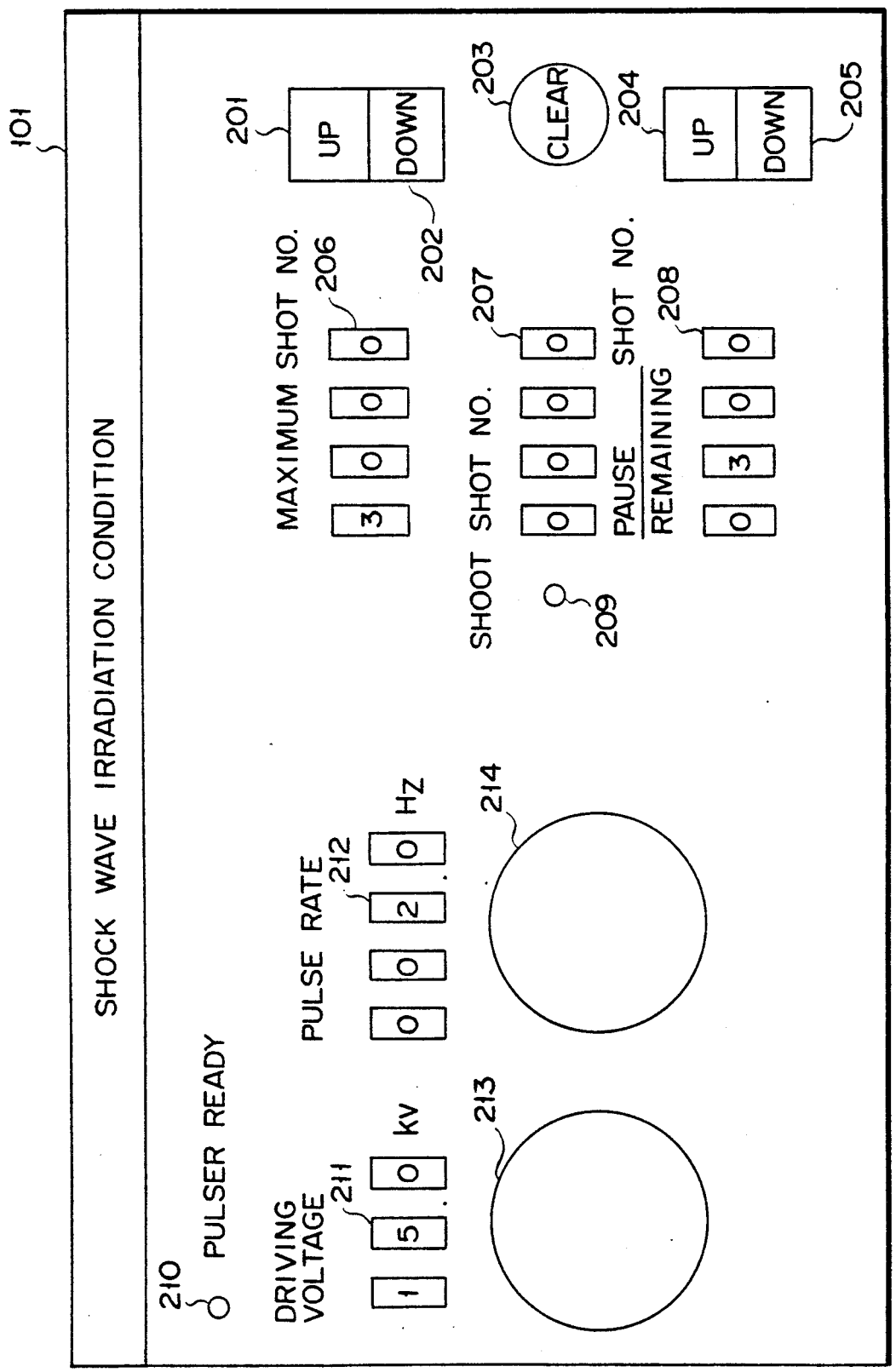
FIG. 3 is a diagram presenting the layout of a console panel of a setting unit of the present system.

The layout of a console panel (not shown) of the setting unit 101 will be described referring to FIG. 3. Shock wave irradiation conditions to be set include the number of shock wave irradiations, a shock wave driving voltage, a pulse rate, and the number of pause shots, as mentioned above.

The number of shock wave irradiations is set by using shock wave irradiation setting buttons, i.e., an UP button 201 and a DOWN button 202. Every time the UP button 201 or DOWN button 202 is pushed, the number of shock wave irradiations is increased or decreased by 100. When the number of shock wave irradiations is set to 3000, an indicator (Maximum Shot No.) 206 displays "3000". This FIGURE remains on the indicator 206 until the number of shock wave irradiations is changed or cleared.

The number of pause shots is set by pause setting buttons, i.e., an UP button 204 and a DOWN button 205. Each pushing of the button 204 or 205 increases or decreases the number of pause shots by 100. When the number of pause shots is set to 300, an indicator (Pause/Remaining Shot No.) 208 displays "300," which counts down by 1 upon each irradiation of a shock wave. That is, the indicator 208 shows the remaining number of pause shots during shock waves are irradiated. When the indicator 208 displays "0", the irradiation is stopped. The indicator 208 is set again to the set value "300" when the irradiation is temporarily stopped.

The shock wave driving voltage is set in the kV range by rotating a driving voltage setting dial 213. When the shock wave driving voltage is set to 15 kV, a driving voltage indicator (Driving Voltage) 211 displays "15.0".

The pulse rate is set by the order of 0.5 Hz by rotating a pulse rate setting dial 214. If the pulse rate is 2 Hz, a pulse rate indicator 212 displays "002.0".

An indictor 207 shows the actual number of shock wave irradiations, and this FIGURE increases by 1 every time a shock wave is irradiated. Upon each shock wave irradiation, a SHOOT lamp 209 is turned on. When the shock wave therapy system is not ready to irradiate a shock wave, a PULSER READY lamp 210 is turned off. A CLEAR button 203 is used to clear the set values of the shock wave irradiation conditions.

The output unit 102 will now be described. The output unit 102 can be a printer. This output unit 102 prints out a therapy record as shown in FIG. 4, for example. In the therapy record, the portion ① presents a graph showing the relation between the driving voltage and the number of shock wave irradiations from the first shot to the 1000th shot. Likewise, the portions ②, ③ and ④ present graphs showing the relation between the driving voltage and the number of shock wave irradiations from the 1001th shot to the 2000th shot, from the 2001th shot to the 3000th shot, and from the 3001th shot to the 4000th shot. The vertical and horizontal scales can be changed in accordance with the shock wave irradiation conditions.

The therapy record includes the shock wave irradiation conditions and patient information. For instance, the patient information (patient ID) has a patient name, the position of the patient's calculus, the size thereof, etc. The patient information is input from a keyboard (not shown).

As can be seen from FIG. 4, the driving voltage is increased to a set value (15 kV) from 0 for every 300 shots of shock waves. This FIGURE "300" is the number of pause shots and shock wave irradiation is temporarily stopped for every 300 shots. After shock wave irradiation is temporarily stopped and a focus point is moved (see FIG. 6), the driving voltage used in the next shock wave irradiation is gradually increased form a zero level. The technique provides increased safety for the patient. When the number of shock wave irradiations ranges from 1 to 4000, for example, the driving voltage is increased by 1 kV to a desired voltage every four shots. When the number of shock wave irradiations ranges from 4001 to 8000, for example, the driving voltage is increased by 1 kV to the desired voltage every eight shots. This method of irradiating shock waves can be set as an irradiation condition.

The operation of the shock wave therapy system according to this embodiment will be described.

When the shock wave applicator 17 is placed on the surface of a patient by an operator and the present shock wave therapy system is operated, an ultrasonic tomographic image, shock wave irradiating region 41, and focus point marker 26 are displayed by the display unit 103. Calculus probing is executed by moving the shock wave applicator 17 according to the displayed image.

Figure 5A:
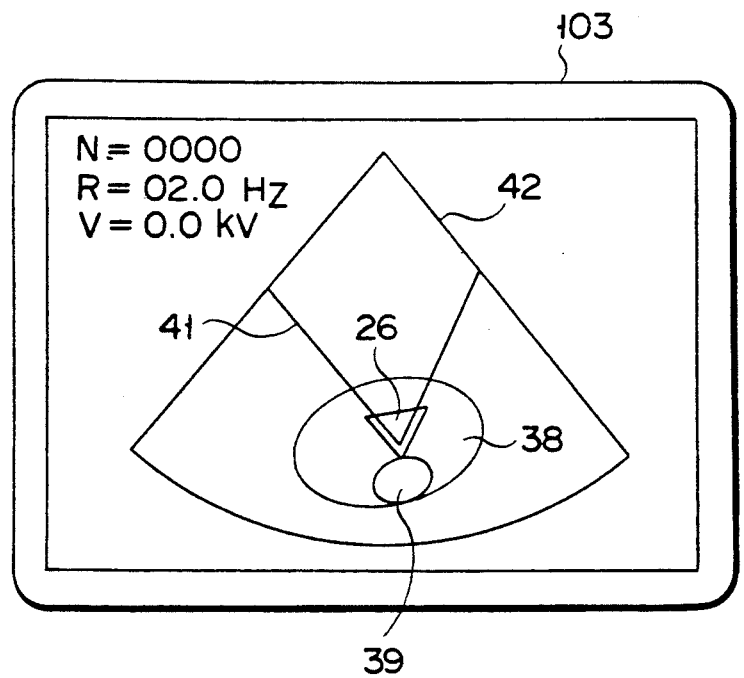
FIGS. 5A and 5B are diagrams showing an image displayed on a display unit of the present system.

When a calculus is detected, the shock wave irradiation conditions are set by the setting unit 101 in accordance with the position and size of the calculus. For example, when the number of shock wave irradiations is 3000, the pulse rate is 2.0 Hz, the driving voltage is 15 kV and the number of pause shots is 300, irradiation condition data representing the shock wave irradiation conditions is displayed on the upper left of the screen of the display unit 103 (see FIG. 5A). In this diagram, N is the actual number of shock wave irradiations also shown on the indicator 207 of the setting unit 101; $N=0$ because FIG. 5A shows an image on the display unit 103 before irradiation of shock waves. The pulse rate R is a constant value (for example, 2 Hz) during shock wave irradiation. The driving voltage V varies during the shock wave irradiation; $V=0$ because no shock waves have been irradiated yet.

When a predetermined switch included in the switch 29 is on after the irradiation conditions are set, shock wave irradiation starts according to the set irradiation conditions. The irradiation condition data displayed on the display unit 103 frequently changes during shock wave irradiation. When the number of shock wave irradiations reaches the number of pause shots (300), the shock wave irradiation is temporarily stopped. In this time, the displayed image may be stored in memory by an image memory apparatus (not shown). The focus point of shock waves is moved while referring to the ultrasonic tomographic image and irradiation condition data displayed on the display unit 103. For instance, the focus point is moved to ② from ① in FIG. 6. After moving the focus point, the irradiation of shock waves restarts.

Figure 5B:
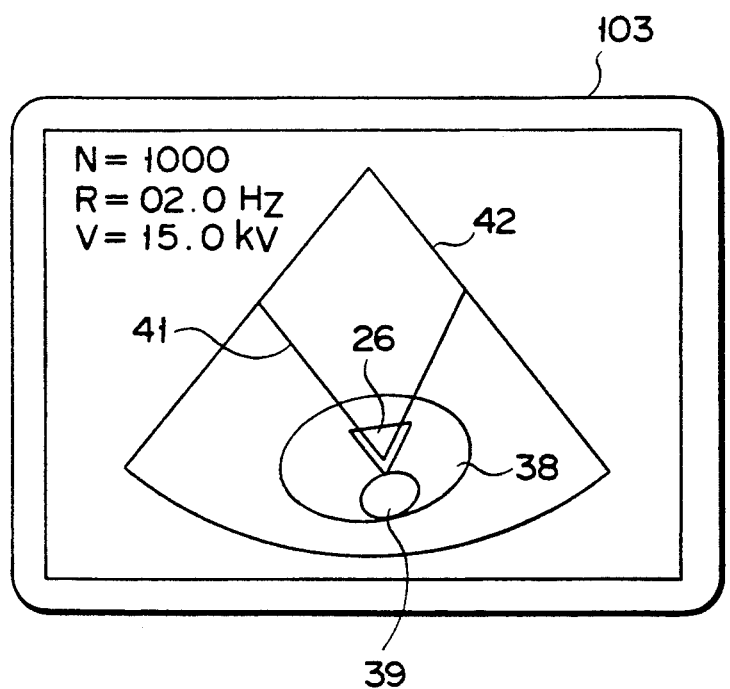

By repetition of the above operation, for example, an image as shown in FIG. 5B is displayed on the display unit 103 during the operation. That is, in the irradiation condition data, the actual number of shock wave irradiations N is 1000, the pulse rate R is 2 Hz and the driving voltage for the 1000 th shot is 15 kV.

When the shock wave irradiation is completed (i.e., the number of shock wave irradiations reaches 3000 in this example), by turning on a predetermined switch included in the switch 29 the aforementioned therapy record (see FIG. 4) is printed out.

Figure 7A:
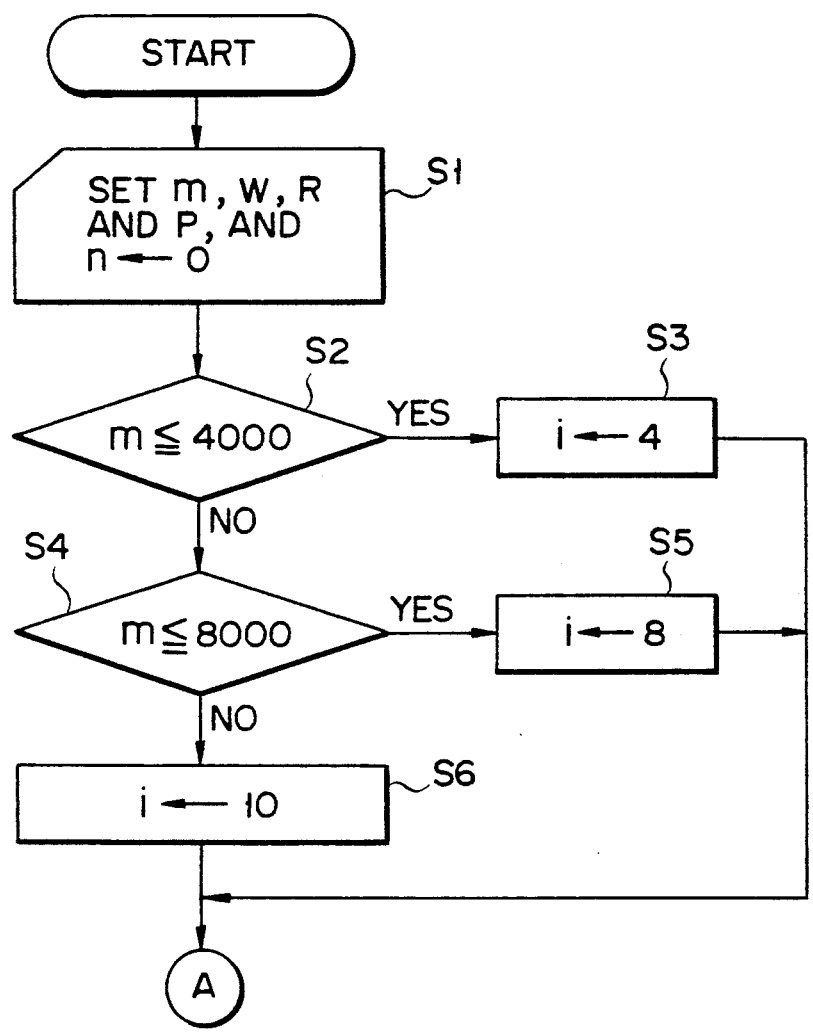
FIGS. 7A and 7B are flowcharts for shock wave irradiation control in the present system.
Figure 7B:
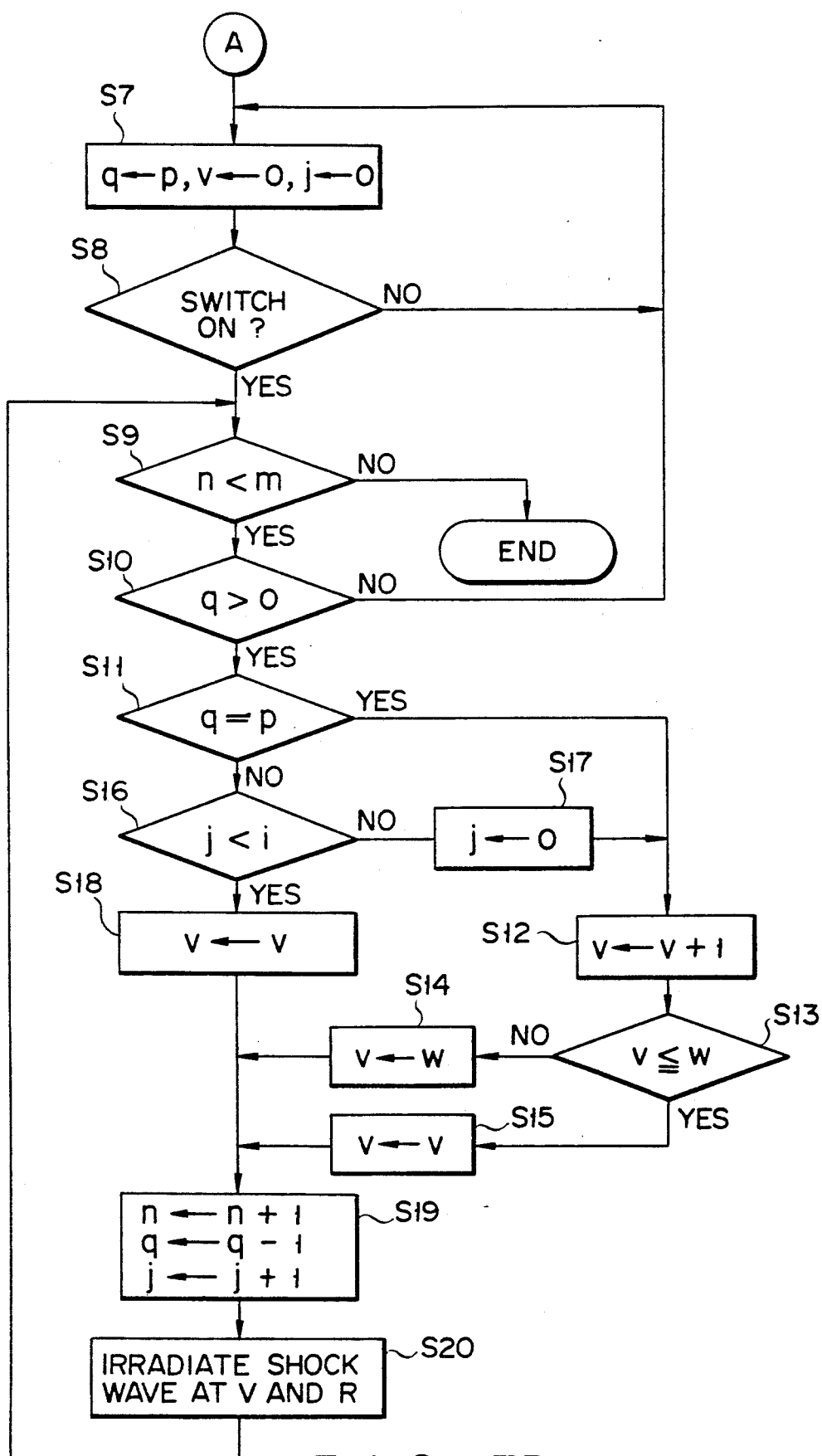

Referring to FIGS. 7A and 7B, the shock wave irradiation control by the CPU 22 of the present shock wave therapy system will be described.

In step S1, the total number of shock wave irradiations m, the maximum driving voltage W, pulse rate R, and the number of pause shots P are set by the setting unit 101. The reference "n" in step S1 indicates the number of shock wave irradiations to be displayed as irradiation condition data on the display unit 103 and is initially set to 0.

In step S2, it is determined whether or not m is equal to or greater than 4000. If $m \leq 4000$, a constant i is set to "4" (step S3). That is, the driving voltage V is increased by, for example, 1 kV for every i shots of shock waves.

In step S4, it is determined whether or not m is equal to or greater than 8000. If $m \leq 8000$, the constant i is set to "8" (step S5). If $m > 8000$, the constant i is set to "10" (step S6).

In step S7, the number of pause shots P is set to a variable q, and the driving voltage V and a variable j are set to 0. The variable q indicates the number of remaining shots until the next pause, and the variable j is used to increase the driving voltage V.

It is determined in step S8 whether or not a shock wave irradiation start switch (not shown) included in the switch 29 is on. If the shock wave irradiation start switch is on, the actual number of shock wave irradiations n is compared with the total number of shock wave irradiations m in step S9.

If n≧m in step S9, the shock wave irradiation is completed. If n≧m, it is determined whether or not the variable q reaches 0 (step S10).

If q=0 in step S10, the shock wave irradiation is temporarily stopped and the processing of step S7 is repeated. If q>0, variable q is compared with the number of pause shots P (step S11).

If q=P in step S11, it is determined that the irradiation control has just started or it is the first irradiation control after a pause. Accordingly, the driving voltage V is increased by 1 kV (step S12). In the step S13, the increased driving voltage V is compared with the maximum driving voltage W which has been set i advance. In other words, the driving voltage at the time of irradiating a shock wave is determined.

If V>W in step S13, the driving voltage for irradiating a shock wave is set to the maximum driving voltage W in order to prevent the driving voltage from being set larger than the maximum driving voltage W (step S14). If V≦W, the increased driving voltage V is set as the driving voltage for irradiating a shock wave (step S15).

If q is not equal to P in step S11, the variable j is compared with the constant i (step S16).

If j<i in step S16, the driving voltage V is set as the driving voltage for irradiating a shock wave (step S18). That is, the driving voltage is not increased. If j≧0, j is set to 0 (step S17). As a result, the driving voltage V is increased by 1 kV (step S12) and the driving voltage for irradiating a shock wave is then determined as described above (step S13).

After the driving voltage for irradiating a shock wave is determined in the above manner, n and j are increased by 1 and f is decremented by 1 (step S19).

In step S20, a shock wave is irradiated once at the set driving voltage V and set pulse rate R. In other words, a command signal for shock wave irradiation is input to the controller 23 and a shock wave is irradiated once under the control of the controller 23. Data representing the driving voltage, the number of shock wave irradiations, etc. which are changed during shock wave irradiation is displayed on the display unit 103 upon each updating of data.

As described above, by the use of the setting unit for setting shock wave irradiation conditions in the shock wave therapy apparatus according to the embodiment of the present invention, it is possible to make a long-term therapy plan and carry out therapy based on the therapy plan, thus obtaining a high margin of safety.

Further, the effect of the therapy can be accurately grasped and a more effective therapy plan can be made by referring to an ultrasonic tomographic image and data representing the shock wave irradiation parameters corresponding to this tomographic image, both displayed on the display unit. Also, the displayed information may be usefully recorded by a video camera, and a therapy record with additional patient information may be displayed on the display unit and/or printed out by the output unit.

Furthermore, by gradually increasing the driving voltage for irradiating a shock wave, a therapy with a high margin of safety can be performed, and by setting the number of pause shots, excess irradiation of shock waves or unnecessary shock wave irradiation can be prevented.

The present invention is not limited to the above embodiment. For instance, the irradiation energy of a shock wave can be set as a shock wave irradiation condition, or only some of the aforementioned conditions can be set.

An ultrasonic tomographic image and data representing shock wave irradiation states corresponding to this image are displayed almost simultaneously with a display time lag within a range of several milliseconds.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A system for controlling shock wave irradiation in a shock wave therapy apparatus, the system comprising:

acquiring means for acquiring an ultrasound tomogram image of a subject;

displaying means for displaying the acquired ultrasound tomogram image to detect a portion to be irradiated within the subject.

irradiating means for irradiating shock waves to the detected portion;

first setting means for setting a maximum number of irradiations of the shock waves;

second setting means for setting a number of pause irradiations of the shock waves; and controlling means for controlling the irradiating means in accordance with the maximum number of irradiations of the shock waves and the number of pause irradiations of the shock waves to irradiate the shock waves to the detected portion during a plurality of irradiation periods determined by the maximum number of irradiations of the shock waves and the number of pause irradiations of the shock waves.

2. The system according to claim 1, wherein the displaying means displays the maximum number of irradiations of the shock waves and the number of pause irradiations of the shock waves corresponding to the displayed ultrasound tomogram image during irradiation of the shock waves.

3. The system according to claim 1, further comprising means for outputting an irradiation record representing an irradiation result after irradiation of the shock waves to the detected portion is completed.

4. The system according to claim 1, wherein the system further comprises:

third setting means for setting a pulse rate of the shock waves; and fourth setting means for setting a driving voltage that generates the shock waves.

5. The system according to claim 4, wherein the system further comprises means for gradually increasing the driving voltage.

6. A system for controlling shock wave irradiation in a shock wave therapy apparatus, the system comprising:

acquiring means for acquiring na ultrasound tomograph image of a subject;

displaying means for displaying the acquired ultrasound tomogram image to detect a portion to be irradiated within the subject;

first setting means for setting a maximum number of irradiations of shock waves;

second setting means for setting a number of pause irradiations of the shock waves;

irradiating means for irradiating shock the waves to the detected portion; and controlling means for controlling the irradiating means in accordance with the maximum number of irradiations of the shock waves and the number of pause irradiations of the shock waves, to irradiate the shock waves to the detected portion during a desired irradiation period, wherein the displaying means displays the maximum number of irradiations of the shock waves and the number of pause irradiations of the shock waves corresponding to the displayed ultrasound tomogram image during irradiation of the shock waves.

7. The system according to claim 6, further comprising means for outputting the image displayed by the displaying means.

8. The system according to claim 6, wherein the system further comprises:

third setting means for setting a pulse rate of the shock waves; and fourth setting means for setting a driving voltage that generates the shock waves.

9. The system according to claim 8, wherein the system further comprises means for gradually increasing the driving voltage.

10. A system for controlling shock wave irradiation in a shock wave therapy apparatus, the system comprising:

acquiring means for acquiring na ultrasound tomograph image of a subject;

displaying means for displaying the acquired ultrasound tomogram image to detect a portion to be irradiated within the subject;

first setting means for setting a maximum number of irradiations of shock waves;

second setting means for setting a number of pause irradiations of the shock waves;

irradiating means for irradiating shock the waves to the detected portion;

controlling means for controlling the irradiating means in accordance with the maximum number of irradiations of the shock waves and the number of pause irradiations of the shock waves, to irradiate the shock waves to the detected portion during a desired irradiation period; and outputting means for outputting an irradiation record representing an irradiation result after irradiation of the shock waves to the detected portion is completed.

11. The system according to claim 10, wherein the system further comprises:

third setting means for setting a pulse rate of the shock waves; and fourth setting means for setting a driving voltage that generates the shock waves.

12. The system according to claim 11, wherein the system further comprises means for gradually increasing the driving voltage.

13. A method for controlling shock wave irradiation in a shock wave therapy apparatus, the method comprising steps of:

acquiring an ultrasound tomogram image of a subject;

displaying the acquired ultrasound tomogram image to detect a portion to be irradiated within the subject;

setting a maximum number of irradiations of shock waves;

setting a number of pause irradiations of the shock waves; and irradiating the shock waves to the detected portion in accordance with the maximum number of irradiations of the shock waves and the number of pause irradiations of the shock waves during a plurality of irradiation periods.

14. The method according to claim 13, wherein the displaying step includes the step of displaying the maximum number of irradiations of the shock waves and the number of pause irradiations of the shock waves corresponding to the displayed ultrasound tomogram image during irradiation of the shock waves.

15. The method according to claim 13, further comprising a step of outputting na irradiation record representing an irradiation result after irradiation of the shock waves to the detected portion is completed.

16. The method according to claim 13, wherein the method further comprises steps of:

setting a pulse rate of the shock waves; and setting a driving voltage that generates the shock waves.

17. The method according to claim 16, wherein the method further comprises a step of gradually increasing the driving voltage.

18. A method for controlling shock wave irradiation in a shock wave therapy apparatus, the method comprising steps of:

acquiring an ultrasound tomogram image of a subject;

displaying the acquired ultrasound tomogram image to detect a portion to be irradiated within the subject;

setting a maximum number of irradiations of shock waves;

setting a number of pause irradiations of the shock waves; and irradiating the shock waves to the detected portion in accordance with the maximum number of irradiations of the shock waves and the number of pause irradiations of the shock waves during a desired irradiation period, wherein the displaying step includes the step of displaying the maximum number of irradiations of ht shock waves and the number of pause irradiations of the shock waves corresponding to the displayed ultrasound tomogram image on a screen during irradiation of the shock waves.

19. The method according to claim 18, further comprising a step of outputting the image displayed on the screen.

20. The method according to claim 18, wherein the method further comprises steps of:

setting a pulse rate of the shock waves; and setting a driving voltage that generates the shock waves.

21. The method according to claim 20, wherein the method further comprises a step of gradually increasing the driving voltage.

22. A method for controlling shock wave irradiation in a shock wave therapy apparatus, the method comprising steps of:

acquiring an ultrasound tomogram image of a subject;

displaying the acquired ultrasound tomogram image to detect a portion to be irradiated within the subject;

setting a maximum number of irradiations of shock waves;

setting a number of pause irradiations of the shock waves;

irradiating the shock waves to the detected portion in accordance with the maximum number of irradiations of the shock waves and the number of pause irradiations of the shock waves during a desired irradiation period; and outputting an irradiation record representing an irradiation result after irradiation of the shock waves to the detected portion is completed.

23. The method according to claim 22, wherein the method further comprises steps of:

setting a pulse rate of the shock waves; and setting a driving voltage that generates the shock waves.

24. The method according to claim 23, wherein the method further comprises a step of gradually increasing the driving voltage.

* * * * *

UNITED STATES PATENT AND TRADEMARK OFFICE
CERTIFICATE OF CORRECTION

PATENT NO. : 5,150,713
DATED : September 29, 1992
INVENTOR(S) : Kiyoshi Okazaki

It is certified that error appears in the above-identified patent and that said Letters Patent is hereby corrected as shown below:

Claim 6, column 8, line 64, change "na" to --an--.

Claim 6, column 8, line 64 and 65, change "tomograph" to --tomogram--.

Claim 6, column 9, line 5, change "shock the" to --the shock--.

Claim 10, column 9, line 34, change "na" to --an--.

Claim 10, column 9, line 34 and 35, change "tomograph" to --tomogram--.

Claim 10, column 9, line 43, change "shock the" to --the shock--.

Claim 15, column 10, line 20, change "na" to --an--.

Claim 18, column 10, line 49, change "ht" to --the--.

UNITED STATES PATENT AND TRADEMARK OFFICE
CERTIFICATE OF CORRECTION

PATENT NO. : 5,150,713
DATED : September 29, 1992
INVENTOR(S) : Kiyoshi Okazaki

It is certified that error appears in the above-indentified patent and that said Letters Patent is hereby corrected as shown below:

Claim 1, column 8, line 27, change "subject."
to --subject;--

Signed and Sealed this

Twenty-fifth Day of October, 1994

Attest:

BRUCE LEHMAN

Attesting Officer

Commissioner of Patents and Trademarks